(12) United States Patent
Fisher et al.

(10) Patent No.: US 6,366,797 B1
(45) Date of Patent: Apr. 2, 2002

(54) METHOD AND SYSTEM FOR BRAIN VOLUME ANALYSIS

(75) Inventors: Elizabeth Fisher, Cleveland Heights; Richard A. Rudick, Solon, both of OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/382,056

(22) Filed: Aug. 24, 1999

Related U.S. Application Data

(60) Provisional application No. 60/097,929, filed on Aug. 25, 1998.

(51) Int. Cl.[7] .............................................. A61B 5/00
(52) U.S. Cl. ...................... 600/410; 382/128; 128/922
(58) Field of Search ................................ 600/410, 407; 382/128, 190, 195, 199, 203, 173; 128/920, 922; 324/309

(56) References Cited

U.S. PATENT DOCUMENTS

| | | | | |
|---|---|---|---|---|
| 5,109,868 A | * | 5/1992 | Smith et al. ................. | 128/774 |
| 5,185,809 A | * | 2/1993 | Kennedy et al. ............... | 382/6 |
| 5,262,945 A | * | 11/1993 | DeCarli et al. .......... | 364/413.13 |
| 5,309,923 A | * | 5/1994 | Leuchter et al. ............ | 128/731 |
| 5,361,763 A | | 11/1994 | Kao et al. | |
| 5,425,368 A | | 6/1995 | Brandt | |
| 5,768,413 A | * | 6/1998 | Levin et al. ................. | 382/173 |
| 5,812,691 A | * | 9/1998 | Udupa et al. ................ | 382/128 |
| 5,859,891 A | * | 1/1999 | Hibbard ........................ | 378/62 |
| 5,937,083 A | * | 8/1999 | Ostuni ......................... | 382/181 |
| 6,047,090 A | * | 4/2000 | Makram-Ebeid ............ | 382/257 |

* cited by examiner

Primary Examiner—Marvin M. Lateef
Assistant Examiner—Shawna J Shaw
(74) Attorney, Agent, or Firm—Calfee, Halter & Griswold, LLP

(57) ABSTRACT

A method of analyzing medical image data to measure brain atrophy and determine the severity and progression of multiple sclerosis or other condition which leads to neurodegeneration or axonal damage is provided. Magnetic resonance image data representing a brain of a subject is provided and a brain surface contour is automatically identified by separating the brain from other connected structures in the image data. A total volume within the brain surface contour is calculated. A brain volume is then determined within the surface contour which excludes fluid filled regions and accounts for partial volume effects. The brain volume is then normalized by the total contour volume which generates a brain parenchymal fraction. The brain parenchymal fraction serves as a reliable measurement of brain atrophy and assists in determining the severity and progression of multiple sclerosis or other condition which leads to neurodegeneration or axonal damage.

20 Claims, 3 Drawing Sheets

METHOD AND SYSTEM FOR BRAIN VOLUME ANALYSIS

This application claims benefit of Provisional Appln. No. 60/097,929 filed Aug. 25, 1998.

BACKGROUND OF THE INVENTION

The present invention relates to medical image analysis arts. It finds particular application to a method and system for analyzing brain volume from magnetic resonance images for measuring brain atrophy and quantitative multiple sclerosis disease evaluation and will be described with particular reference thereto. Of course, it will be appreciated that the present invention will also find application to the analysis of medical images obtained from other medical imaging systems capable of imaging the brain, and for quantitative evaluation of other conditions which lead to neurodegeneration or axonal damage.

Magnetic resonance imaging (MRI) offers high contrast images which are far superior to those of other imaging modalities in terms of anatomical detail. In addition, flexible imaging sequences and choices of image orientation allow for detailed analysis of the brain, and for computer methods which can accurately segment the brain into cerebral spinal fluid (CSF), gray matter and white matter compartments.

To date, a number of quantitative MRI methods have reported measurements of cerebral spinal fluid, gray and white matter volumes in brain. Three general methods have been employed: (1) operator directed outlining of a region of interest (ROI); (2) special sequences to enhance cerebral spinal fluid and suppress brain matter signals; and (3) segmentation routines which utilize either automatic boundary outlining or threshold determinations.

Although tracing a region of interest can be quick and simple, it is the most operator intensive, and requires extensive training as well as a detailed knowledge of neuroanatomy. Special MRI sequences have been designed to selectively enhance the cerebral spinal fluid signal for volume determination, but it is not clear how partial volume averaging is accounted for with those sequences. Moreover, the MRI images generated are not suitable for standard radiological interpretation. Semi-automatic boundary outlining or thresholding routines are usually time consuming, and require the operator to select "seed" pixel values to choose numerical thresholds, or to sample representative pixel intensity values for brain and cerebral spinal fluid segmentation. The requirement for operator interaction leads to variable results due to differences in human perception.

The segmentation of the brain in magnetic resonance (MR) images is essential for quantitative analysis in clinical applications. Highly accurate and precise segmentation is required for serial studies which depend on repeated measurements over time for the detection of small changes. For example, for treatment evaluation in multiple sclerosis (MS), quantification of brain atrophy and lesion volumes in MR images is often used in conjunction with clinical evaluation to provide more objective measures of MS burden. Most current methods of quantification incorporate subjective techniques such as manual counting of lesions in 2D slices, or manual tracing for calculating areas and volumes. These segmentation methods may yield intra- and inter-operator variability rates which are higher than the expected changes to be measured. Therefore, computer-aided approaches have been designed to improve reliability. Brain segmentation is essential to determination of the brain volume. It is also important in surface-based registration since the segmented brain surface can be used for alignment of serial images acquired at different times. For these reasons, an automated segmentation technique is necessary to fully exploit the quantitative capabilities of MR imaging.

Automated segmentation of brain structures and tissues in MR is complicated by several factors. The overlap of gray level characteristics of different tissue-types precludes the use of global thresholding as a stand-alone segmentation technique. Typically, there are also inter- and intra-slice nonuniform intensity variations due to RF and/or receiver inhomogeneities which must be handled. Partial volume effects, due to the averaging of signals from different tissues sampled in the same voxel, result in voxels which can not be classified as any one particular type. For highest possible accuracy, an ideal segmentation technique should take all three of these factors into account. The segmentation should also be flexible in order to accommodate images from a variety of MR pulse sequences. Since the relative intensities of tissues vary according to each particular pulse sequence, a purely intensity-based strategy may not be flexible in this regard.

Techniques for "automated" segmentation of brain MR images have been developed to address these problems and to minimize manual interaction. Generic algorithms, such as multi-spectral clustering or thresholding combined with connectivity operations, still usually require the user to select appropriate thresholds or training sets to identify tissues, which can lead to significant variability in the results. Even with methods in which the parameters are determined automatically, anatomic structures connected to the brain and of similar intensity pose problems for thresholding/connectivity-based algorithms of this type, and often require manual editing at the end. Knowledge-based methods attempt to solve these problems by using anatomic information to drive the segmentation to fit some a priori model of the brain. However, the model assumptions are often overly restrictive, especially since there is significant diversity in anatomic features of the brain in different pathological conditions, and considerable differences in the intensity characteristics arising from different MR image acquisition techniques.

The present invention provides a new and unique method and system for fully automated brain image analysis, which solves the above problems and others for the evaluation of multiple sclerosis and other conditions that lead to neurodegeneration and/or axonal damage.

SUMMARY OF THE INVENTION

A method of analyzing magnetic resonance images of a brain to determine the severity and progression of a medical condition is provided. Magnetic resonance images of a brain are provided. A brain surface contour is identified from the magnetic resonance image data. A total volume within the brain surface contour is calculated. A brain volume within the brain surface contour is then determined. The severity of a medical condition is evaluated based on a ratio of the brain volume to the total contour volume.

In accordance with another aspect of the present invention, a method of determining brain atrophy from image data of a brain obtained from a magnetic resonance imaging system is provided. The image data represents brain tissue and non-brain regions of a subject. A surface contour of the brain is determined in the image data. A total volume is determined within the surface contour and a brain volume is determined that is the total contour volume less a volume of the non-brain regions within the surface contour. A brain parenchymal fraction is generated which is the brain volume normalized by the total contour volume. Brain atrophy is then determined according to the brain parenchymal fraction.

One advantage of the present invention is that it provides a reproducible and reliable measurement of brain atrophy by eliminating the subjective analysis of brain image data.

Another advantage of the present invention is that it provides a reliable measurement of brain volume changes over time such that an assessment of brain atrophy and the progression of multiple sclerosis or other condition which leads to neurodegeneration or axonal damage can be made. In this regard, the brain volume from the image data is analyzed in three-dimensions and normalized, which partially eliminates errors in volume determination caused by patient repositioning.

The normalization results in an additional advantange for cross-sectional studies. Since the normalized brain volume is within a constant range for healthy individuals, the present invention can be also be used to measure brain atrophy in individuals at a single point in time.

Another advantage of the present invention is that it provides a method for whole brain atrophy measurement rather than measuring atrophy in multiple sclerosis which measures only ventricular volumes or individual slice volumes. This is important in diffuse diseases in order to account for the total effects of the disease on brain tissue.

Another advantage of the present invention is that it provides a fast method for calculating brain volumes. With current hardware technology, the present invention takes approximately 2.5 minutes on a standard UNIX workstation to segment the entire brain in a set of 30 magnetic resonance images.

Still further advantages of the present invention will become apparent to those of ordinary skill in the art upon reading and understanding the following detailed description of the preferred embodiments.

BRIEF DESCRIPTION OF THE DRAWINGS

The following is a brief description of each drawing used to describe the present invention, and thus, are being presented for illustrative purposes only and should not be imitative of the scope of the present invention, wherein.

DETAILED DESCRIPTION OF THE PREFERRED EMBODIMENTS

Figure 1:
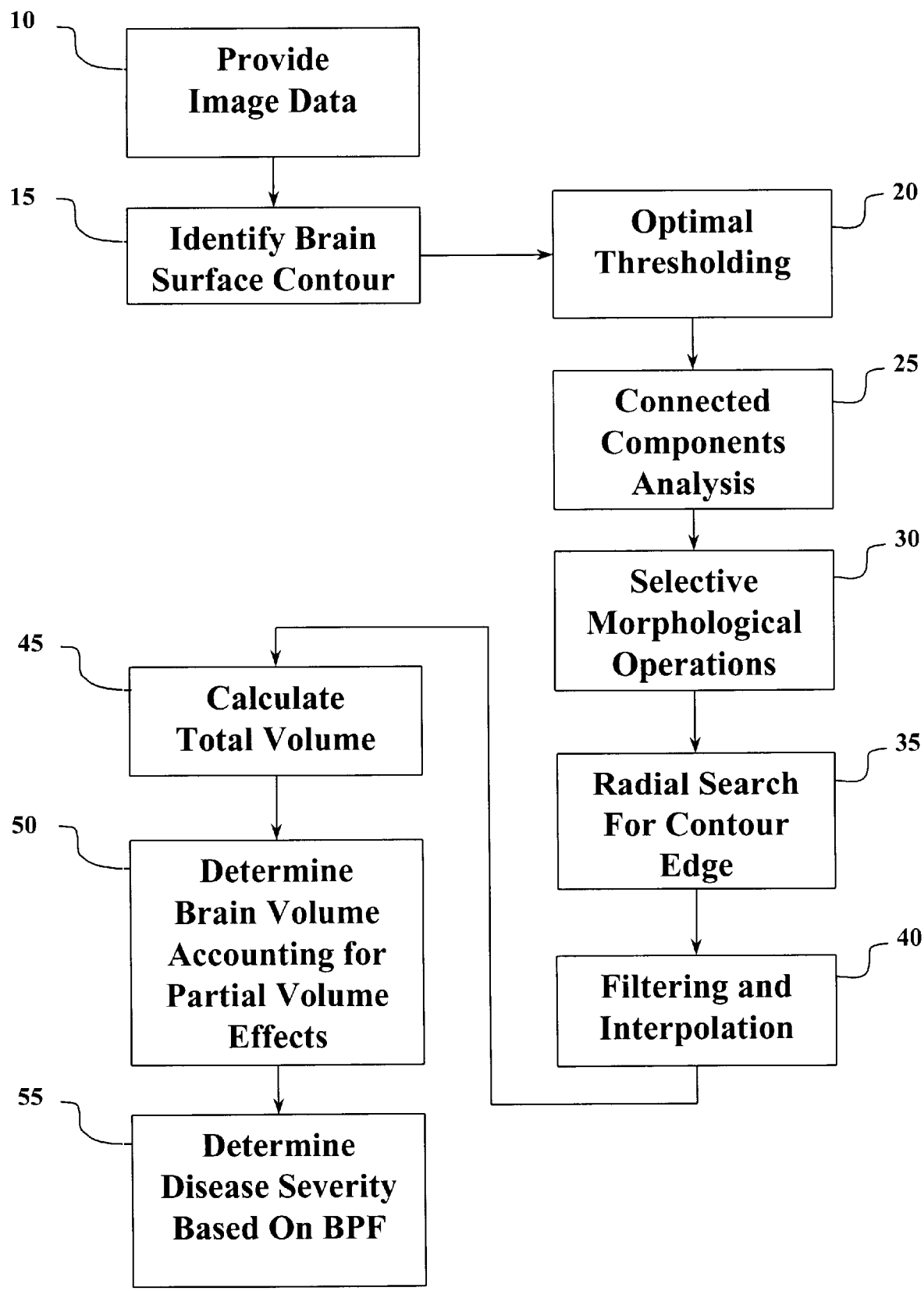
FIG. 1 illustrates a process of analyzing image data in accordance with the present invention.
Figure 2A:
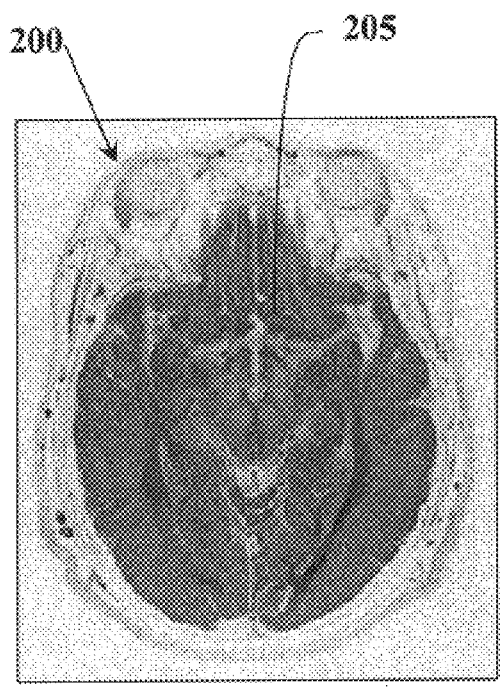
FIGS. 2a–2e illustrate intermediate segmentation images for one exemplary image data slice in accordance with the present invention.

With reference to FIG. 1, a process for analyzing medical image data in accordance with the present invention is shown. In the preferred embodiment, the present system and process is a software-implemented process executed by a computer. It will be appreciated that any portion or all of the software functions may be hardware implemented. Medical images of a brain are obtained and acquired 10 by any suitable medical imaging system such as a magnetic resonance imaging system as is known in the art. Exemplary image data is shown in FIG. 2a which is an image slice representing a subject's head 200 and brain 205. In the preferred embodiment, the image data are a set of two-dimensional image slices covering the entire brain and are analyzed as one three-dimensional data set. FIGS. 2a–2e show one exemplary image data slice as it appears during intermediate stages of the present processing.

Figure 2B:
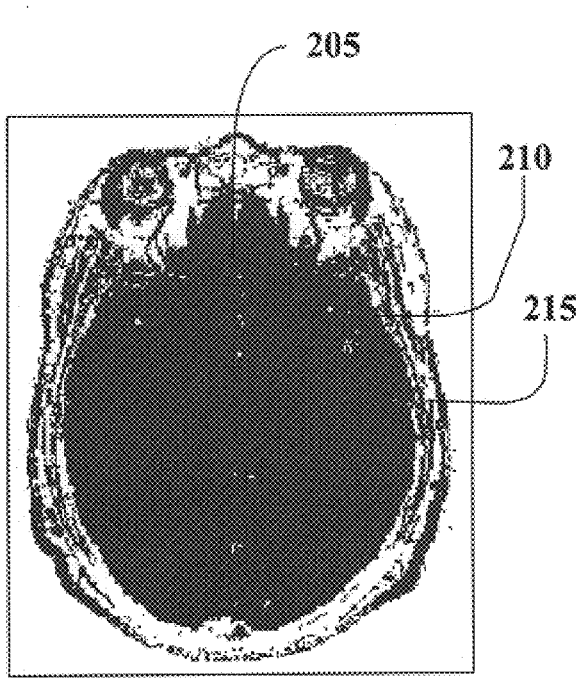

The image data are analyzed to identify 15 the surface contour 210 of the brain 205. This is performed by first identifying the brain 205 in the image data by separating "object" from "background" by optimal thresholding 20. Preferably, a minimum error threshold is determined using histogram statistics which separates a mixture of two populations modeled as Gaussian distributions. In this case, a conservative threshold is automatically selected which insures that brain tissue is not omitted from the image data. The original image set is then median filtered for noise removal and thresholded. FIG. 2b illustrates the image data slice as it may appear after thresholding where the highlighted regions represent the "object" which was not eliminated by the thresholding step. The "object" includes the brain 205 and possibly additional connected objects, such as the eyes and optic nerve, that are not part of the brain. The brain is also surrounded by other structures such as the cranium, scalp, etc.

To initially separate the brain 205 from non-brain regions, a sequence of alternating connected components analysis and morphological operations are performed. First, connected components analysis 25 is performed to label the "largest connected structure" in the image data as "brain" and all other bright structures as "other". Selective morphological erosion 30 is performed on the brain-labeled region to partially isolate the brain from other connected structures as is known in the art. A 3×3×3 diamond-shaped kernel is applied to the image data to remove small connections stemming from the "largest connected structure" further isolating the brain. In other words, the kernel turns off small groups of pixels around the edges of the brain surface which connect non-brain structures to the brain, thus, disconnecting the non-brain structures. Of course, there are many types of kernels that can be used for this step. The connected components analysis 25 is repeated to re-label any newly disconnected structures as "other" and the selective morphological dilation is again performed on the brain-labeled region. It will be appreciated that these steps may be performed once or as many times as desired to isolate the brain from non-brain regions. After this processing, there may still be some structures connected to the brain which need to be removed.

Figure 2C:
Figure 2D:

A three dimensional radial search 35 is performed in spherical space to find brain surface contour points at the edge of the intra-cranial cavity (ICC) 215 which marks the brain surface contour edge 210. The ICC is a fluid filled region between the brain and surrounding structures which is detectable in at least some portions of the image. The search begins at the centroid of the brain-labeled region. In spherical coordinates, a $\rho$ value is sought for each $(\theta,\psi)$ which specifies the radial distance from the centroid to the edge of the brain. Each voxel occurring at a pattern of "brain-background" is labeled as an edge and its radial distance from the centroid is stored in a two dimensional map of radius values. Based on the labeling described above, when a specific pattern of "brain-background-other" is encountered in the image data, the edge voxel is re-labeled as a possible ICC edge point. At locations where there are connected structures, the pattern is not found, so not all radial lines will contain an ICC edge point. FIG. 2c illustrates an edge contour 220 determined from the ICC edge points found by the radial search. The radius values are then bi-linearly interpolated based on neighboring values to fill in the two dimensional map of radius values.

The edge information from the two dimensional map is used to define the brain surface contour edge by finding the strongest edges. Edge "strengths" are calculated and stored, where the strength of an edge is equivalent to the weighted sum of other edge points and ICC points found within a pre-defined l×m×n neighborhood of pixels. That is, $$edge\ strength = \frac{\sum_{(\theta=-l)}^{l} \sum_{(\phi=-m)}^{m} \sum_{(\rho=-n)}^{n} edge_{\theta,\phi,\rho}}{2 \times l \times m} \quad (1)$$

where $$edge_{\theta,\phi,\rho} = \begin{cases} 0 & \text{if no edge point was found at } (\theta, \phi, \rho) \\ 1 & \text{if an edge point, but not an } ICC \text{ point was found at } (\theta, \phi, \rho) \\ 2 & \text{if an } ICC \text{ point was found at } (\theta, \phi, \rho) \end{cases} \quad (2)$$

and the neighborhood size is dependent on the type of magnetic resonance image. After median filtering the two dimensional (θ, ψ) map to smooth the ICC contour points, bilinear interpolation is performed to fill in the missing ρ values. In some areas, a large portion of the ICC must be interpolated 40. Since the brain is not spherical, it is possible that the interpolation would exclude portions of the brain in these areas. To ensure that the true ICC points are found, for each interpolated location the local region along the radial line is searched for the strongest edge point. This step locates the ICC and "cuts off" any remaining connected structures producing a resultant ICC surface contour 220 shown in FIG. 2d. The voxels which are located within the resultant ICC surface contour and meet the threshold criteria of the first step are taken as the first estimate to the segmented brain tissue.

Since the image data is three-dimensional and includes multiple image slices, interslice intensity variations and partial volume effects are analyzed and corrected if necessary. First, the mean intensity values for the brain and background are calculated for each slice individually and for the whole set of images. The ratio of the means of these two populations is taken as the multiplicative correction factor for each slice:

$$correction factor_{slice} = \frac{ave(\mu_{bckgd}, \mu_{brain})global}{ave(\mu_{bckgd}, \mu_{brain})slice} \quad (3)$$

Partial volume corrections are based on a two-compartment model. The model assumes that each voxel near the edge of the brain may contain up to two tissue classes, brain and cerebral spinal fluid (CSF). Using the class averages for each of these two compartments, the contribution of each class can be calculated from the measured voxel intensity. That is, if the measured intensity, I, is considered to be $$I = a\mu_{CSF} + b\mu_{brain} \quad (4)$$

then the proportion of brain tissue, b, is simply, $$b = \frac{(\mu_{CSF} - I)}{(\mu_{brain} - \mu_{CSF})} \quad (5)$$

Figure 2E:
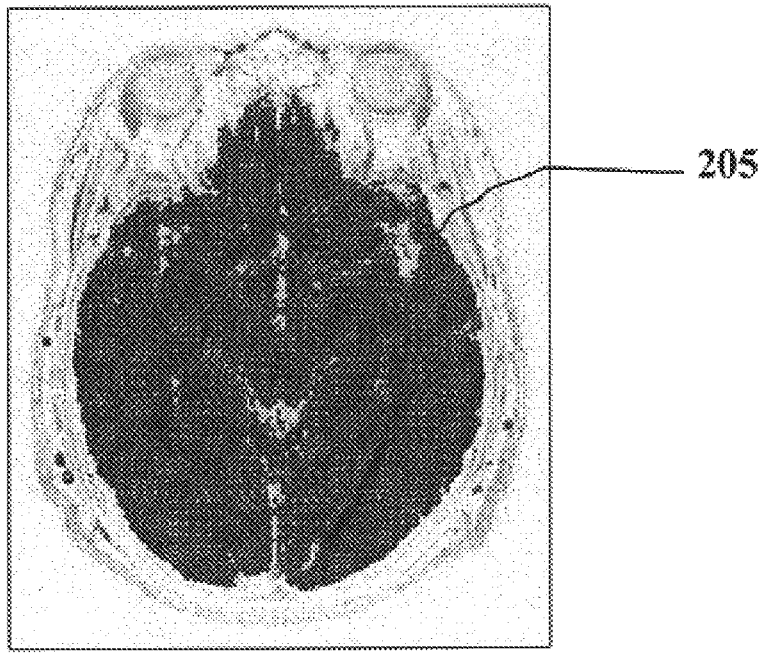

An exemplary segmented brain mask is shown in FIG. 2e.

Figure 3:
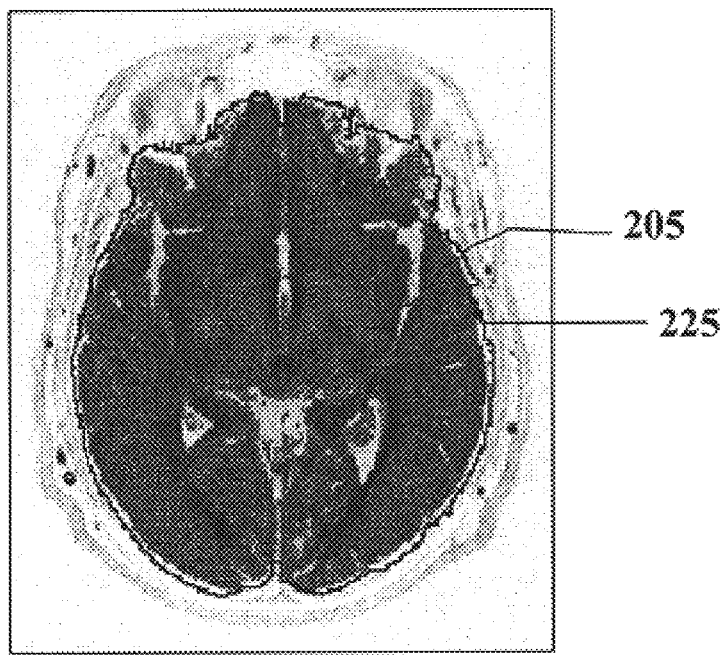
FIG. 3 illustrates the final segmentation results for one exemplary image data slice in accordance with the present invention.

With further reference to FIG. 1, after the brain surface contour is determined, the total volume contained within the brain surface contour is calculated at 45. The total contour volume includes the volumes of all regions within the contour whether they represent brain tissue or not. The brain tissue volume is then determined 50 which includes three tissue classes, namely, normal brain tissue, lesions, and partial volume voxels. The volume of a voxel in the image data that overlaps both tissue and non-tissue is adjusted to more accurately represent only the partial volume that overlaps tissue. Thus, the brain tissue volume is determined using a finite mixture density model to account for partial volume effects according to equation (5) above. This model is used to determine the fractional contribution of each segmented voxel within the contour which lies on the border between brain and CSF regions. Voxels representing fluid filled regions within the surface contour are not included in the brain tissue volume. The final results for an exemplary slice are shown in FIG. 3, with the total contour volume composed of all voxels within the red contour, and the brain volume represented by the voxels included in the blue transparent overlay.

A brain parenchymal fraction (BPF) is calculated as a ratio of the brain tissue volume to the total volume contained within the brain surface contour. In other words, the brain tissue volume is normalized by the total contour volume. The severity and progression of a medical condition which leads to neurodegeneration or axonal damage is determined 55 based on the BPF value. The present inventors have found that normal subjects have a similar BPF. In tests, a group of normal subjects, who did not have a medical condition, were found to have a BPF within a range of 0.86 to 0.88 and a mean BPF of 0.871 with a standard deviation of 0.0077. Since the brain tissue volume is normalized by the total contour volume, all normal subjects have a similar BPF because factors such as head size are offset by the normalizing step. Additionally, the normalizing offsets errors which might occur when determining the brain surface contour such as including non-brain structures within the contour. It should be appreciated that the normal range of BPF may change once a greater population of subjects are tested.

For evaluation of disease progression, a BPF below the normal range indicates brain atrophy and may be a surrogate marker of the severity of a medical condition such as multiple sclerosis, brain tissue damage caused by a medical condition, or other conditions which lead to neurodegeneration or axonal damage. For example, assuming a subject is known to have a medical condition such as multiple sclerosis, comparing the subject's BPF to a predetermined normal BPF range can determine the severity of brain tissue damage caused by the medical condition. If the BPF ratio is within the predetermined normal range, the severity of brain tissue damage is negligible. If the ratio is below the predetermined normal range, the severity of brain tissue damage is significant. In tests, subjects with multiple sclerosis had a mean BPF of 0.821 with a standard deviation of 0.0656 which is below the range of normal subjects. Some multiple sclerosis subjects had a BPF as low as 0.699 which is well below the range of normal subjects and indicated severe brain atrophy.

The measurement of brain atrophy based on the BPF provides a highly reproducible measurement of atrophy which is consistent among healthy individuals. Results show that there is a significant difference in the atrophy measures between a normal group and a multiple sclerosis group which are well matched for gender and age. By obtaining and analyzing image data from the same subject over time, the BPF provides a reliable measure of atrophy regardless of how the image data was obtained, the image views, or position of the subject during imaging. Changes in a subject's BPF over time is used to measure the rate of brain atrophy and to assess the severity of brain tissue damage.

It will be appreciated that many conditions can cause an abnormally low BPF besides multiple sclerosis including normal aging, high blood pressure, hydrocephalus, stroke, Alzheimer's, anorexia, steroid use, alcohol abuse, etc. The BPF can serve as a surrogate marker of disease severity not only in MS but other neurodegenerative diseases and conditions.

The invention has been described with reference to the preferred embodiment. Obviously, modifications and alterations will occur to others upon a reading and understanding of this specification. It is intended to include all such modifications and alterations insofar as they come within the scope of the appended claims or the equivalence thereof.

We claim:

1. A method of analyzing magnetic resonance images of a brain to determine severity of a medical condition comprising the steps of:

providing magnetic resonance image data representative of the brain;

identifying a brain surface contour from the magnetic resonance image data;

calculating a total contour volume within the brain surface contour;

determining a brain volume within the brain surface contour; and evaluating the severity of the medical condition based on a ratio of the brain volume to the total contour volume.

2. The method of analyzing magnetic resonance images as set forth in claim 1 wherein calculating the brain volume includes excluding non-brain regions within the brain surface contour from the total contour volume and accounting for partial volume effects.

3. The method of analyzing magnetic resonance images as set forth in claim 2 wherein the non-brain regions include fluid filled regions within the brain surface contour.

4. The method of analyzing magnetic resonance images as set forth in claim 1 wherein identifying the brain surface contour includes:

thresholding the image data to include brain tissue within the image data;

labeling connected components in the image data, a largest connected component being labeled as the brain; and searching radially in the image data from within the largest connected component to determined an edge of the largest connected component, the edge representing the brain surface contour.

5. The method of analyzing magnetic resonance images as set forth in claim 4 wherein the searching includes:

searching radially for edges of the largest connected component in a plurality of directions to determine brain surface contour points; and filtering and interpolating the brain surface contour points in spherical space to define the brain surface contour and to exclude non-brain structures connected to the brain.

6. The method of analyzing magnetic resonance images as set forth in claim 1 wherein evaluating the severity of the medical condition includes comparing the ratio to a predetermined range where if the ratio is within the predetermined range, the severity of brain tissue damage caused by the medical condition is mild, and if the ratio is below the predetermined range, the severity of brain tissue damage caused by the medical condition is significant.

7. The method of analyzing magnetic resonance images as set forth in claim 6 wherein the medical condition is a neurodegenerative disease.

8. The method of analyzing magnetic resonance images as set forth in claim 1 further including:

determining a rate of brain atrophy by comparing the ratio with a second ratio of brain volume to total contour volume generated from a second set of image data of the brain, the second set of image data being obtained subsequent to the image data.

9. A method of determining brain atrophy from image data of a brain obtained from a magnetic resonance imaging system, the image data representing brain tissue and non-brain regions of a subject, the method comprising the steps of:

determining a surface contour of the brain in the image data;

determining a total contour volume within the surface contour;

determining a brain volume being the total contour volume less a volume of the non-brain regions within the surface contour;

generating a brain parenchymal fraction being the brain volume normalized by the total contour volume; and determining brain atrophy according to the brain parenchymal fraction.

10. The method of determining brain atrophy as set forth in claim 9 wherein the volume of the non-brain regions within the surface contour is determined from a volume of fluid filled regions.

11. The method of determining brain atrophy as set forth in claim 9 wherein the brain volume includes a volume of lesions.

12. The method of determining brain atrophy as set forth in claim 9 wherein the determining brain atrophy according to the brain parenchymal fraction includes comparing the brain parenchymal fraction to a predetermined value.

13. The method of determining brain atrophy as set forth in claim 12 wherein the predetermined value represents a ratio of the brain volume to the total contour volume of a healthy brain.

14. The method of determining brain atrophy as set forth in claim 13 wherein the comparing indicates significant brain tissue damage if the brain parenchymal fraction is less than the predetermined value.

15. The method of determining brain atrophy as set forth in claim 14 wherein the predetermined value is in a range of 0.86 to 0.88.

16. The method of determining brain atrophy as set forth in claim 9 wherein determining the surface contour includes:

thresholding the image data to remove background data;

identifying the brain within the image data; and identifying outer edges of the brain within the image data, the outer edges defining the surface contour of the brain.

17. The method of determining brain atrophy as set forth in claim 9 wherein determining brain atrophy includes measuring a rate of brain atrophy by comparing the brain parenchymal fraction to a previously generated brain parenchymal fraction from the same subject.

18. A method of measuring brain atrophy from image data representing a brain of a subject, the method comprising the steps of:

defining a contour in the image data which contains the brain;

calculating a total contour volume contained within the contour; determining a brain volume within the contour, the brain volume excluding regions representing non-tissue regions and accounting for partial volume effects;

normalizing the brain volume with the total contour volume; and measuring brain atrophy by comparing the normalized brain volume to a predetermined value.

19. The method of measuring brain atrophy as set forth in claim 18 wherein the predetermined value represents a healthy normalized brain volume.

20. The method of measuring brain atrophy as set forth in claim 18 wherein the predetermined value is calculated from a plurality of healthy normalized brain volumes.

* * * * *